(12) United States Patent
Werner et al.

(10) Patent No.: US 10,765,069 B2
(45) Date of Patent: Sep. 8, 2020

(54) SUPPLEMENTING SUB-OPTIMAL ENVIRONMENTAL CONDITIONS TO OPTIMIZE PLANT GROWTH

(71) Applicant: International Business Machines Corporation, Armonk, NY (US)

(72) Inventors: John S. Werner, Fishkill, NY (US); Anuradha Rao, Hopewell Junction, NY (US); Pasquale A. Catalano, Wallkill, NY (US); Arkadiy O. Tsfasman, Wappingers Falls, NY (US); Andrew G. Crimmins, Montrose, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 299 days.

(21) Appl. No.: 15/982,230

(22) Filed: May 17, 2018

(65) Prior Publication Data
US 2019/0350140 A1    Nov. 21, 2019

(51) Int. Cl.
*A01G 7/04* (2006.01)
*G10K 11/18* (2006.01)
*G01N 33/00* (2006.01)

(52) U.S. Cl.
CPC ............ *A01G 7/04* (2013.01); *G01N 33/0098* (2013.01); *G10K 11/18* (2013.01)

(58) Field of Classification Search
CPC ....... A01G 7/04; G01N 33/0098; G01K 11/18
USPC .................................................. 47/58.1 LS
See application file for complete search history.

(56) References Cited

U.S. PATENT DOCUMENTS

| 5,731,265 A | 3/1998 | Hou et al. |
| 8,074,397 B2 | 12/2011 | Yoneda et al. |
| 8,689,483 B2 | 4/2014 | Lin et al. |

(Continued)

FOREIGN PATENT DOCUMENTS

| CA | 1190405 A | * | 7/1985 | ............. A01N 45/00 |
| CN | 204480669 U |   | 7/2015 | |

OTHER PUBLICATIONS

Peter Mell et al., "The NIST Definition of Cloud Computing", National Institute of Standards and Technology, Publication No. 800-145, Sep. 2011, 7 pages.

*Primary Examiner* — Magdalena Topolski
*Assistant Examiner* — William L Gmoser
(74) *Attorney, Agent, or Firm* — Cantor Colburn LLP; Teddi Maranzano (57) ABSTRACT

Embodiments include a computer-implemented method, system, and computer program product for supplementing sub-optimal environmental conditions for plant growth, the embodiments include receiving plant data for a plant, and extracting optimal growth condition data from a database based at least in part on the plant. Embodiments also include obtaining sensor data from sensors monitoring current growth conditions of the plant and comparing the current growth conditions of the plant to the optimal growth condition data from the database to estimate a current cytoplasmic streaming rate. Embodiments include responsive to the comparison, calculating, by the calculation engine, a sound wave frequency to stimulate cytoplasmic streaming in the plant, transmitting the sound wave frequency to a speaker, and providing the sound wave frequency to the plant.

20 Claims, 7 Drawing Sheets

(56) References Cited

U.S. PATENT DOCUMENTS

| | | | |
|---|---|---|---|
| 2004/0053353 A1* | 3/2004 | Carpenter | G01N 33/5097 |
| | | | 435/34 |
| 2008/0271372 A1* | 11/2008 | Wang | A01G 7/04 |
| | | | 47/66.6 |
| 2009/0199470 A1* | 8/2009 | Capen | F21K 9/00 |
| | | | 47/58.1 LS |
| 2011/0162116 A1* | 6/2011 | Holman | A01H 3/00 |
| | | | 800/306 |
| 2012/0089201 A1* | 4/2012 | Pilla | A61N 1/40 |
| | | | 607/50 |
| 2013/0060473 A1 | 3/2013 | Tomida | |
| 2014/0352210 A1 | 12/2014 | Redding, Jr. | |
| 2016/0360713 A1* | 12/2016 | Wu | A01G 22/00 |
| 2017/0332544 A1* | 11/2017 | Conrad | A01B 79/005 |
| 2018/0284016 A1* | 10/2018 | Fujiyama | A01G 7/04 |

* cited by examiner

SUPPLEMENTING SUB-OPTIMAL ENVIRONMENTAL CONDITIONS TO OPTIMIZE PLANT GROWTH

BACKGROUND

The present invention generally relates to environmental monitoring systems, and more specifically, to supplementing sub-optimal environmental conditions to optimize plant growth.

Plant and crop productivity is directly affected by changes in environmental conditions such as a change in the weather. Plant and crop productivity increases as cell growth and division occur within the plant. At a basic level, the amount of water and sunlight and soil conditions can impact the growth rate. Plant growth describes an increase in size, leaf and/or flower development, and also in number as more plants begin to grow. Various sensors can be used to monitor one or more conditions of the plant where the conditions can be changed to encourage efficient plant growth.

SUMMARY

Embodiments of the present invention are directed to a computer-implemented method for supplementing sub-optimal environmental conditions to optimize plant growth. A non-limiting example of the computer-implemented method includes receiving plant data for a plant, extracting optimal growth condition data from a database based at least in part on the plant, and obtaining sensor data from sensors monitoring current growth conditions of the plant. The computer-implemented method also includes comparing the current growth conditions of the plant to the optimal growth condition data from the database to estimate a current cytoplasmic streaming rate, and responsive to the comparison, calculating a sound wave frequency to stimulate cytoplasmic streaming in the plant. The computer-implemented method includes transmitting the sound wave frequency to a speaker, and providing the sound wave frequency to the plant.

Embodiments of the present invention are directed to a system for supplementing sub-optimal environmental conditions to optimize plant growth. A non-limiting example of the system includes one or more processors, and at least one memory, the memory including instructions that, upon execution by at least one of the one or more processors, cause the system to perform a method for supplementing sub-optimal environmental conditions for plant growth, where the method includes receiving plant data for a plant, extracting optimal growth condition data from a database based at least in part on the plant, and obtaining sensor data from sensors monitoring current growth conditions of the plant. The method also includes comparing the current growth conditions of the plant to the optimal growth condition data from the database to estimate a current cytoplasmic streaming rate, and responsive to the comparison, calculating a sound wave frequency to stimulate cytoplasmic streaming in the plant. The method includes transmitting the sound wave frequency to a speaker, and providing the sound wave frequency to the plant.

Embodiments of the invention are directed to a computer program product for supplementing sub-optimal environmental conditions to optimize plant growth, the computer program product comprising a computer readable storage medium having program instructions embodied therewith. The program instructions are executable by a processor to cause the processor to perform a method. A non-limiting example of the method includes receiving plant data for a plant, extracting optimal growth condition data from a database based at least in part on the plant, and obtaining sensor data from sensors monitoring current growth conditions of the plant. The method also includes comparing the current growth conditions of the plant to the optimal growth condition data from the database, and responsive to the comparison to estimate a current cytoplasmic streaming rate, calculating a sound wave frequency to stimulate cytoplasmic streaming in the plant. The method includes transmitting the sound wave frequency to a speaker, and providing the sound wave frequency to the plant.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
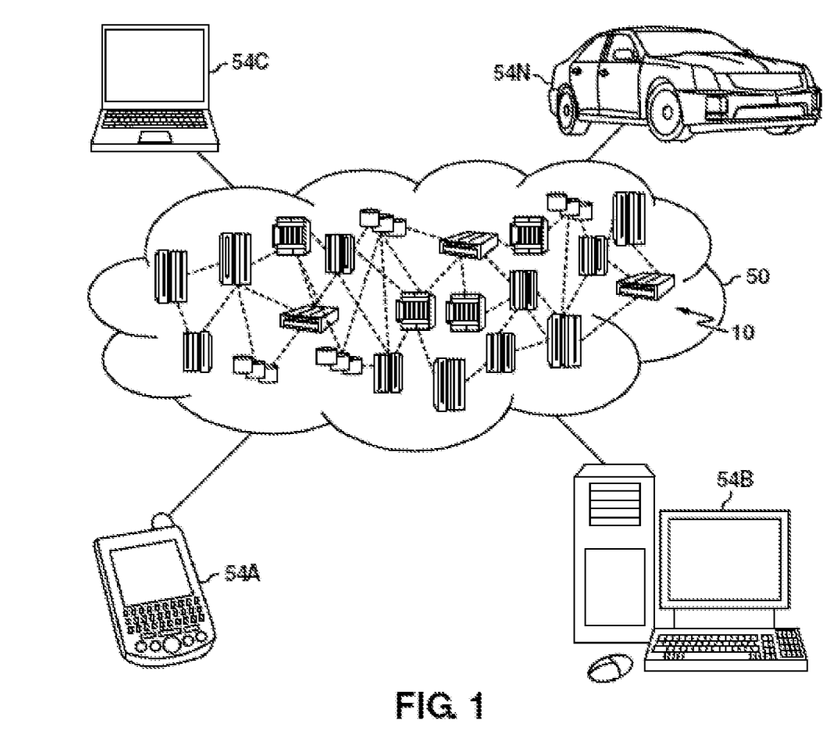
FIG. 1 depicts a cloud computing environment according to one or more embodiments of the present invention.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
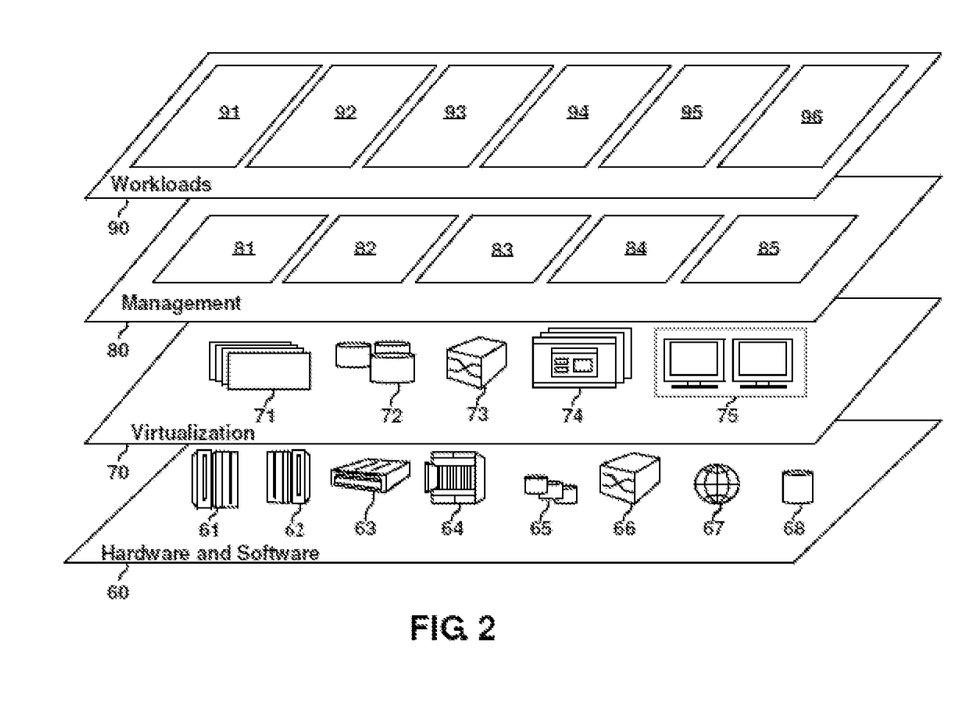
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and action analytics and notifications 96.

Figure 3:
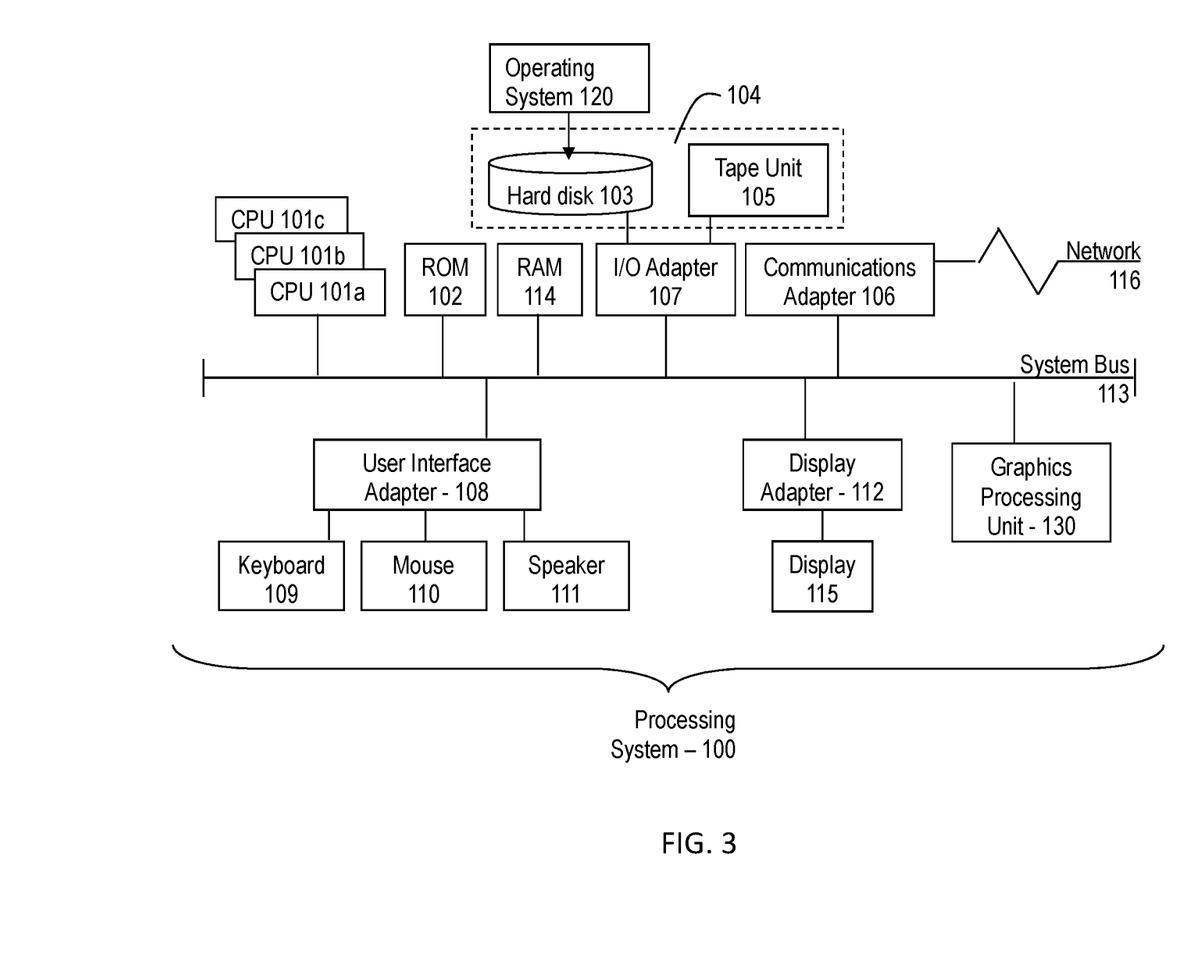
FIG. 3 illustrates a block diagram of a computer system for use in practicing the teachings herein.

Referring to FIG. 3, there is shown an embodiment of a processing system 100 for implementing the teachings herein. In this embodiment, the system 100 has one or more central processing units (processors) 101a, 101b, 101c, etc. (collectively or generically referred to as processor(s) 101). In one or more embodiments, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 3 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing and has a highly parallel structure that makes it more effective than general-purpose CPUs for algorithms where processing of large blocks of data is done in parallel.

Thus, as configured in FIG. 3, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system coordinate the functions of the various components shown in FIG. 3.

Turning now to an overview of technologies that are more specifically relevant to aspects of the invention, various sensors and devices have been used to monitor conditions of different types of environments and control processes. For example, sensors can be used to obtain data indicating the performance, where the collected data can be used to control the output of a sound wave frequency that can optimize plant growth.

One or more embodiments of the invention are directed to monitoring and controlling plants' productivity in their environment. Many factors can impact the rate of plant growth. For example, the amount and intensity of sunlight, air temperature and humidity, soil pH and other soil characteristics, carbon dioxide levels, and water intake all impact the processes occurring within a plant. In addition, every plant has different genetic make-up and has different nutritional/environmental requirements that can also affect the growth rate. Plant and crop productivity increases when photosynthesis occurs at an increased rate.

Environmental conditions may exist that impact the behavior and rate of cytoplasmic streaming in a plant which are not optimal for plant growth. Cytoplasmic streaming refers to the directed flow of cytosol (the liquid component of the cytoplasm) and organelles around fungal and plant cells. By controlling or altering the cytoplasmic streaming, the delivery of organelles, nutrients, metabolites, genetic information, and other materials to different parts of the cell is optimized allowing for more molecules to travel within the cell and get collected by chloroplasts.

By increasing the number of molecules collected by the chloroplasts, photosynthesis will be directly impacted. Light reactions occur when light energy is captured and pushed into a chemical called adenosine triphosphate (ATP) and dark reactions occur when ATP is used to make glucose during a process known as the Calvin Cycle. Plants use the glucose produced from these reactions for growth.

Undesirable growth conditions can negatively impact the productivity and efficiency in the production of healthy plants and crops. In an effort to increase productivity and plant health, the conditions of the plant can be monitored and adapted to encourage photosynthesis. For example, increased amounts of water can be provided to plants that did not receive a sufficient amount of water. In another example, if the soil conditions lack nutrients, fertilizer can be added to improve the current conditions of the soil. Other undesirable conditions can be monitored and changed.

The adaptations contribute to increasing the conditions for photosynthesis which is affected by the cytoplasmic streaming occurring in the plant as described above. One or more embodiments of the invention are directed to controlling the rate of cytoplasmic streaming occurring in a given plant to encourage consistent photosynthesis in the plant.

Turning now to an overview of the aspects of the invention, one or more embodiments of the invention address the above-described shortcomings of the prior art by providing a technique to impact the rate of cytoplasmic streaming, by inducing vibrations in the plant, to supplement the sub-optimal environmental conditions the plant is exposed to.

One or more embodiments of the invention monitor conditions surrounding a growing plant including plant type, temperature, humidity, soil pH levels, sunlight intensity, etc. to improve the current growth conditions to increase plant productivity. Subsequently, the differences between the optimal growth conditions and the current monitored conditions for the given plant or crop type are calculated. Responsive to the calculated difference, an optimal sound wave frequency or music that contains that optimal frequency is determined to supplement the suboptimal environmental conditions to induce vibrations to stimulate the plant and alter the cytoplasmic streaming within the plant. The vibrations are induced using a speaker that is located in proximity of the plant. The speaker is configured to play a calculated sound wave frequency or music centered around the calculated sound wave frequency. In one or more embodiments, the music can be accessed from a playlist of a user over a network. The calculation and selection is based on decreasing the rate of cytoplasmic streaming in harsh conditions and increasing the rate of cytoplasmic streaming in conditions that are too mild.

The above-described aspects of the invention address the shortcomings of the prior art by implementing a plant environmental monitoring system and a plant tracking and growth optimization device to calculate sound wave frequencies to increase the plant growth rate. The calculated sound wave frequencies are provided to the plant and monitored over time. In one or more embodiments of the invention, data can be leveraged from other user's that have grown or experimented with the same/similar plants. In addition, the calculated sound wave frequency, plant type, and additional information can be stored for future reference.

Figure 4:
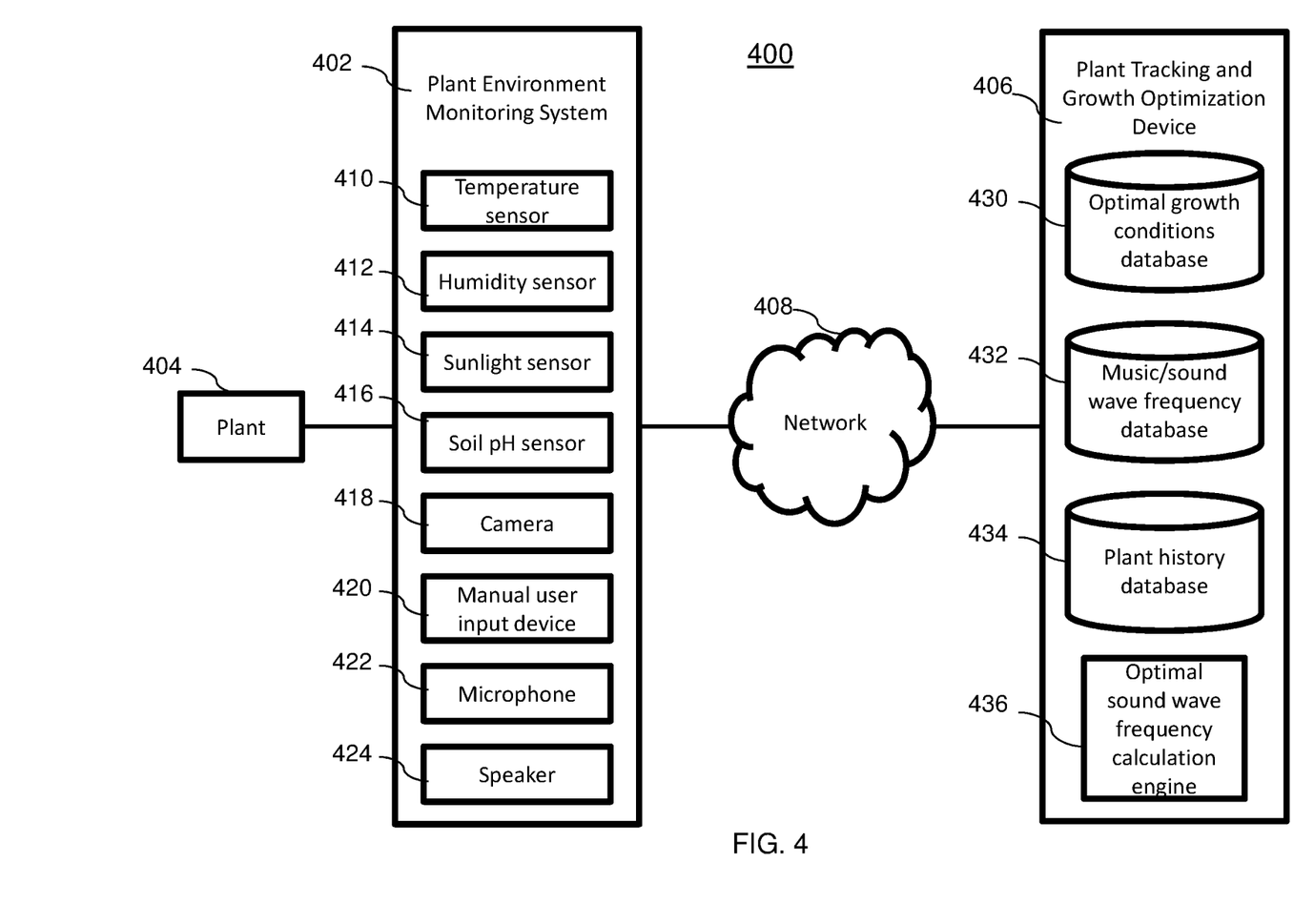
FIG. 4 depicts a plant optimization system for supplementing sub-optimal environment conditions to optimize plant growth in accordance with one or more embodiments of the invention.

Turning now to a more detailed description of aspects of the present invention, FIG. 4 depicts a system 400 for supplementing sub-optimal environmental conditions to optimize plant growth according to embodiments of the invention.

The plant environment monitoring system 402 is configured to monitor a plant 404. In addition, the plant environment monitoring system 402 exchanges data with the plant tracking and growth optimization device 406. In one or more embodiments of the invention, the plant environment monitoring system 402 communicates with the plant tracking and growth optimization device 406 over a network 408. The network 408 can include a wired or wireless network or a combination thereof.

As shown in FIG. 4, the plant environment monitoring system 402 includes a plurality of components, modules, sensors, equipment, devices, etc. In one or more embodiments, the system 402 includes one or more temperatures sensors 410, humidity sensors 412, sunlight sensors 414, and soil pH sensors 416. Sensors are positioned proximate the plant 404 that is being monitored to determine the actual conditions the plant 404 is exposed to. The sunlight sensors 414 can measure the amount of sunlight, sunlight intensity, and/or sunlight wavelength. In addition to the soil pH, the soil moisture, soil salinity, and soil nutrients can be monitored. The carbon dioxide levels can also be monitored.

In addition, the system 402 includes an image capturing device 418 to identify the plant 404 being monitored and to monitor the development of the plant 404. The image capturing device 418 can use images of the plant 404 to perform a search in a database to match an identity of the plant 404 and to monitor changes in the growth and development of the plant over time. The system 402 also includes a user input device 420 where the user can provide inputs regarding the type of plant 404, conditions experienced by the plant 404, etc. A microphone 422 and speaker 424 can also be included in the system 402. The microphone 422 can be used to determine the current sound conditions in the vicinity of the plant 404 or to verify the speaker 424 is functioning properly. The microphone 422 can be used to ensure the calculated frequency sound wave (discussed below) is outputting the correct frequency. The speaker 424 is used to provide a particular sound wave frequency to the plant. In one or more embodiments, the speaker 424 can be positioned above ground and/or below ground. In addition, the distance and volume of the speaker 424 are controlled and factored into the calculation of the sound frequency wave to stimulate vibrations and cytoplasmic streaming of the plant 404 in a predictable manner. The sound wave frequency is calculated to create a resonance in the plant to supplement sub-optimal growth conditions. In one or more embodiments of the invention, the timbre of the sound wave frequency may be altered in increased plant growth.

It is to be understood that other sensors, devices, processors, and the like can be included in the system and FIG. 4 provides a non-limiting example of the devices and data that are monitored.

The plant tracking and growth optimization device 406 includes and/or communicates with a plurality of databases. Also, the plant tracking and growth optimization device 406 includes an optimal sound wave frequency calculation engine.

The databases can include an optimal growth conditions database 430. The data stored in the optimal growth conditions database 430 includes information related to optimal temperature, humidity, sunlight, soil conditions for growth. The optimal growth conditions database 430 also includes frequency response data corresponding to increased cytoplasmic streaming rates for a given plant. The frequency response data can be derived from previous experimentation on the plants, where embodiments of the invention leverage the frequency response data provided from other users provided that the results have been stored in the optimal growth conditions database 430. The frequency response data is used by the optimal sound wave frequency calculation engine 436 (hereinafter referred to as calculation engine 436) to calculate the sound wave frequency to modify the current cytoplasmic streaming rate for the given plant. In one or more embodiments of the invention, the databases 430-434 can be coupled to the plant environment monitoring system 402 over the network 408 and/or be located in a cloud computing environment as shown in FIG. 1 and FIG. 2.

The data included for optimal plant growth has been determined and tested over time through various studies. In addition, as new plants are added and monitored, the desired growth condition data can be included in the optimal growth conditions database 430. Also, the database can be formed from and include experimentation of cytoplasmic streaming levels for a given plant in different conditions during different parts of the plant's life cycle. Additionally, a cognitive system can be employed to leverage data from other users growing the same/similar plant in the same/similar conditions. In one or more embodiments, a confidence score can be developed based on a number of similar conditions providing similar results. The confidence score can be provided to the users. The cognitive system can adjust sound wave frequency based on the confidence score until an optimal sound wave frequency is learned for a given plant in known conditions dependent upon the plants age or state in its growth cycle.

A music/sound wave frequency database 432 can also be included in the plant tracking and growth optimization device 406. In addition, the music/sound wave frequency database 432 can correlate sound wave frequencies to various songs/music that are centered around the calculated frequency from the calculation engine 436. In one or more embodiments of the invention, a user playlist can be accessed where the songs/music of the user are related to various frequencies. The user's playlist can be directly accessed or indirectly accessed over a network through wired and/or wireless means. In some embodiments, the music/sound wave frequency database 432 may be a user account on a music streaming service.

The plant tracking and growth optimization device 406 can also contain a plant history database 434 that stores the previous conditions for a given plant and the sound wave frequencies that were calculated for each plant. In addition, the plant history database 434 can be updated to track the progress and results of plant 404. The database 434 stores and tracks the history and performance of plants over time. In one or more embodiments, the optimal growth condition database 430 may be updated based on a cognitive system analyzing the history and performance of conditions that had positive impacts to a plant 404.

The device 406 also includes a calculation engine 436 to calculate and identify a sound wave frequency that will adjust the cytoplasmic streaming rate of the plant 404 based on comparing the current growth conditions of the plant 404 to the optimal growth conditions. In one or more embodiments, the calculation engine 436 retrieves the known frequency response data for a given plant from one or more databases 430-434. The calculation engine 436 uses the frequency response data to estimate the cytoplasmic streaming data based on experimental/optimal conditions and determines the difference between the optimal cytoplasmic streaming rate and the current estimated cytoplasmic streaming rate. Based on the difference the calculation engine 436 performs calculations for octave ratios and converts the octave ratios to cent values, where the cent values are used to calculate the desired note frequency. The cent is a logarithmic unit of measure used for musical intervals. In one or more embodiments, the calculated frequency is correlated to a musical note or a song that is centered around the calculated frequency. A non-limiting example will be discussed below with reference to FIGS. 5 and 6.

In one or more embodiments of the invention, the sensors include but are not limited to temperature sensors, humidity sensors, sunlight sensors, and pH sensors. In addition, an image capturing device or camera can be used to monitor the plant growth and/or health using visual imaging processing.

In embodiments, the user input device may be used in lieu of a camera where a user can manually input plant size and any other data that may be useful for monitoring plant growth. A microphone is used to monitor environmental noise and to verify the speaker included in the environmental system is functioning properly. The speaker is used to provide various sound wave frequencies to the plant.

The system includes or is operably connected to one or more databases. The databases including an optimal growth conditions database 430 which includes the optimal environmental conditions for a plurality of plants throughout their life cycles, a music/sound wave frequency database 432 which contains the audio files that may be streamed to the speaker, and plant history database 434 which tracks the environmental conditions the plant was subjected to, the music or sound wave frequencies that were played, and the overall growth of the plant.

In one or more embodiments, the monitored environmental conditions and sound wave frequency/music played are stored in a database such that cognitive algorithms can be used to further optimize plant growth in the future by altering the selected sound wave frequency/music if necessary. The databases are shown separately, however, in other embodiments the data and/or databases can be combined into a single database. The music/sound wave frequency database 432 may alternatively exist on the plant environmental monitoring/output device and use a personal music library from the user caring for the plant. Alternatively, the music/sound wave frequency database 432, may exist on an external server operated by a streaming service and may connect to the plant environmental monitoring system 402 via the network 408.

Figure 5:
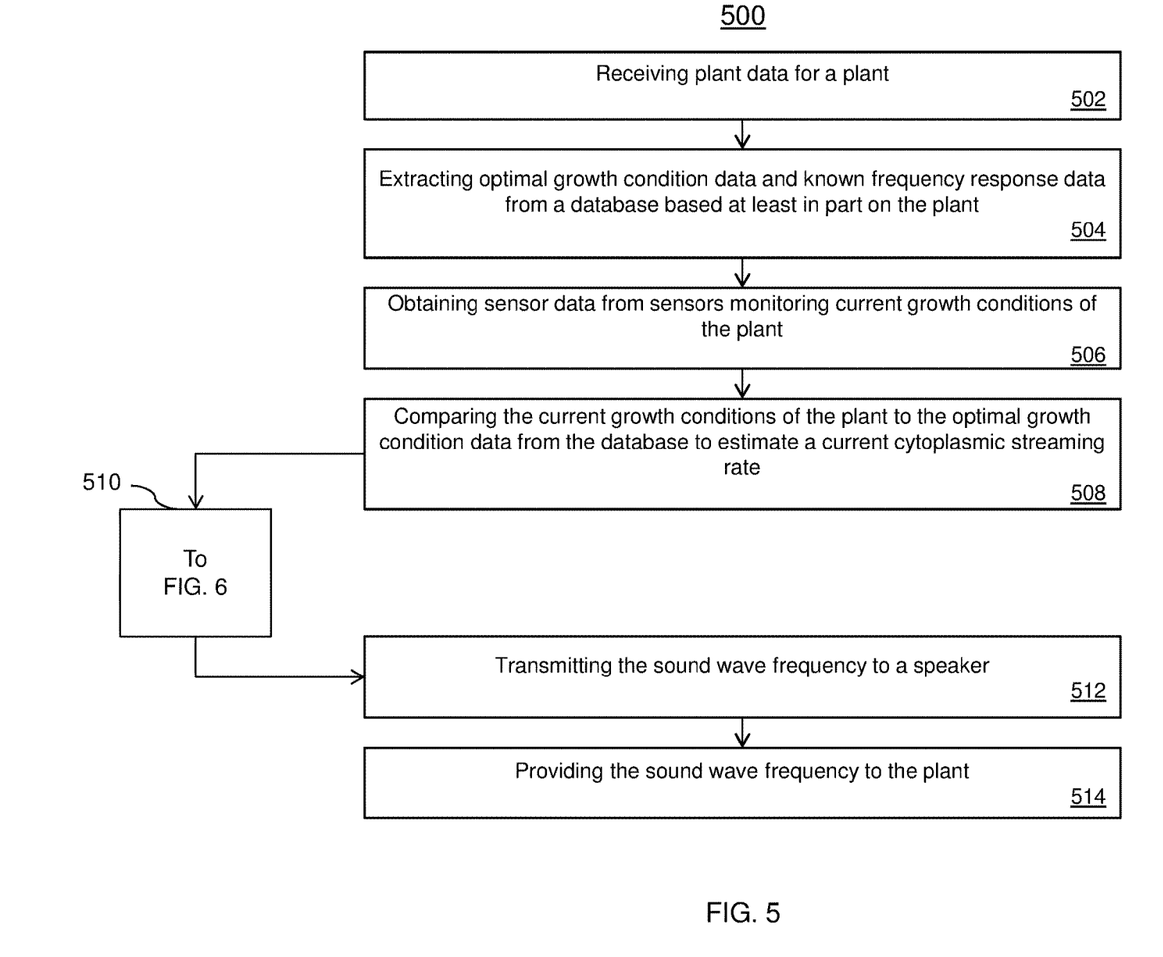
FIG. 5 depicts a flow chart of a method for supplementing sub-optimal environment conditions to optimize plant growth in accordance with one or more embodiments of the invention.

Now referring to FIG. 5, a method 500 for supplementing sub-optimal environmental conditions to optimize plant growth is shown.

The method 500, at block 502, provides for receiving plant data for a plant. The plant data for a given plant identifies the specific plant that is monitored by the system. In other embodiments, plants can be identified by class or type of plant. The plant data can be input into the system by a user or an image of the plant can be obtained by an image capturing device where the image is compared to other plant images to identify the given plant using visual recognition software (e.g., IBM Watson® Visual Recognition API). The plant data also includes data such as the plant type, current size, current point in life cycle, and the like.

Block 504 provides for extracting optimal growth condition data and known frequency response data from a database based at least in part on the plant data. Subsequent to identifying the plant, the optimal growth conditions for the plant are identified. The growth condition information can include temperature, humidity, soil condition, sunlight, etc. It is to be understood that other conditions can be used in determining the optimal growth conditions for the plant. The known frequency response data provides the frequency that encourages the optimal cytoplasmic streaming rate that is based on previous experimentation. The embodiments of the invention leverage this data to perform calculations for the sound wave frequency that is to be used to modify the current cytoplasmic streaming rate of a given plant.

Block 506 provides for obtaining sensor data from the sensors monitoring current growth conditions of the plant. In one or more embodiments of the invention, the environmental conditions of the plant are monitored where the sensors include but are not limited to the sensors discussed above. In one or more embodiments, the first sensor data is collected by the system 400 or the optimization device 406. Then, each of the plurality of sensors' data can be collected to perform the estimated cytoplasmic streaming rate. The sensor data is collected until each and every sensor has been read.

The method 500, at block 508 provides for comparing the current growth conditions of the plant to the optimal growth condition data from the database. The cytoplasmic streaming rate can be estimated based on a percentage difference between the optimal growth condition and a current growth condition. The percentage difference is used to adjust the current cytoplasmic streaming velocity to the optimal cytoplasmic streaming velocity, provided from the database 430 which is based on experimentation. The estimated cytoplasmic streaming velocity is initially assumed to be the optimal cytoplasmic streaming velocity. The estimation is adjusted based on the percentage difference of a sensor reading from the optimal growth conditions specific to the sensor. For example, for a given plant having an optimal temperature condition of 77 degrees, a temperature sensor provides a current reading of 72.4 degrees. The percentage difference is calculated as a 6% difference and will be used to adjust the estimated cytoplasmic streaming rate by 6%. Each of the sensors' readings of the current conditions and the optimal growth conditions from the database 430 are obtained and used to determine a percentage difference which is used to adjust the estimated cytoplasmic streaming rate through each iteration until all of the sensor readings have been accounted for. The comparison determines whether the difference from the optimal growth conditions is within a configurable tolerance or acceptance level. In the event that the current growth conditions are outside of the optimal range, the sub-optimal environmental conditions are supplemented to increase or decrease the cytoplasmic streaming within the plant, thus optimizing photosynthesis and productivity. Further details performed by the calculation engine 436 are described with reference to FIG. 6 described below. In one or more embodiments of the invention, a percentage difference is calculated between the cytoplasmic streaming rate for the current conditions and the optimal cytoplasmic streaming rate for the optimal conditions.

Responsive to calculating the sound wave frequency at block 510, the method 500 proceeds to block 512 and provides for Block 510 provides for calculating, responsive to the comparison, a sound wave frequency to stimulate cytoplasmic streaming in the plant. In one or more embodiments of the invention, when the current environmental conditions for the plant are too harsh, sound wave frequencies (or music) are calculated and provided to the plant to reduce the amount of cytoplasmic streaming. Alternatively, if the environmental conditions for the plant are too tame, sound wave frequencies are calculated and provided to increase cytoplasmic streaming. Cognitive models and machine learning may be utilized to learn the affects that certain sound frequencies have on certain plants in certain conditions such that the calculation engine 436 of FIG. 4 can learn the impacts of different sound wave frequencies such that an optimal sound wave frequency can be calculated at block 510 based on the results of the comparison at block 508.

Responsive to calculating the sound wave frequency at block 510, the method 500 proceeds to block 512 and provides for transmitting the sound wave frequency to a speaker. In one or more embodiments the sound wave frequency can be transmitted through a wired/or wireless means to the speaker. The speaker location and volume are also used in adjusting the cytoplasmic streaming in the plant. The speaker can be placed above and/or below ground. In other embodiments, multiple speakers can be used to provide the sound wave frequency to the plants. Block 514 includes providing the sound wave frequency to the plant.

In one or more embodiments of the invention, the same or similar process can be used on plant seeds as it has been shown that seeds that were exposed to sound wave frequencies (music) and subsequently germinated, produced plants that had more leaves, were greater in size, and other improved characteristics. The stimulation from the sound wave frequency or music causing vibrations in the plant can aid in cell division and repair, which further increases plant growth.

Figure 6:
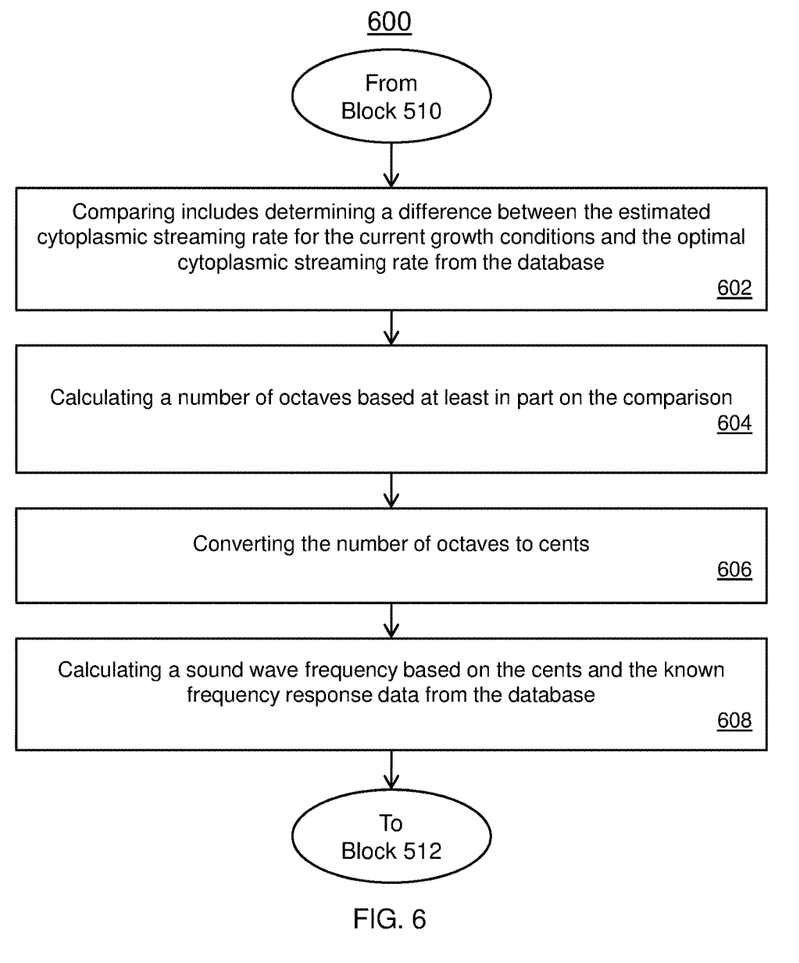
FIG. 6 depicts a flow chart of another method for supplementing sub-optimal environment conditions to optimize plant growth in accordance with one or more embodiments of the invention.

With reference now to FIG. 6, a method 600 performed by the calculation engine 436 is shown. The method 600, at block 602, provides for comparing, from block 510 of FIG. 5, which includes determining a difference between the estimated cytoplasmic streaming rate for the current growth conditions and the optimal cytoplasmic streaming rate form the database. According to Equation 1:

$$\Delta = \text{Optimal} - \text{Estimated} \qquad \text{(Eq. 1)}$$

where optimal=optimal cytoplasmic streaming rate; estimated=cytoplasmic streaming rate.

The method 600 proceeds to block 604 and includes calculating a number of octaves based on the difference from the comparison performed at block 602. To calculate the number of octaves, Equation 2 provides:

$$\text{Octaves} = \frac{\text{Optimal} - \text{Estimated}}{\text{Known}} \qquad \text{(Eq. 2)}$$

where the known value is based on a known condition for a given frequency yielding a particular cytoplasmic streaming rate increase, such as a frequency of 46.249 Hz ($F^{\#}_1$) yielding a cytoplasmic streaming velocity increase of 2 µm/sec for a given plant. The 2 µm/sec is used as the known value.

At block 606, the method 600 provides for converting the number of octaves calculated at block 604 to cents. Recall that cents are a logarithmic unit of measure used for musical intervals. The conversion factor to convert the number of octaves to cents is provided below:

$$\frac{1 \text{ octave}}{1200 \text{ cents}} \quad \text{(Eq. 3)}$$

Block 608 provides for calculating a sound wave frequency based on the cents and the known frequency response data from the database. The calculation in Equation 4 provides:

$$n = 1200 * \log_2\left(\frac{a}{b}\right) \quad \text{(Eq. 4)}$$

where n=cents; a=frequency for a given plant under optimal conditions; b=sound wave frequency. Solving for b Equation 5 provides:

$$b = a \times 2^{n/1200} \quad \text{(Eq. 5)}$$

After calculating the sound wave frequency, the method 600 returns to block 512 of FIG. 5.

In a non-limiting example, after identifying a given plant by techniques described above, a known cytoplasmic streaming velocity for the given plant under optimal conditions can be 50 µm/sec as provided in the optimal growth conditions database 430. It may also be known that a frequency of 46.249 Hz ($F^{\#}_1$) yields a cytoplasmic streaming velocity increase of 2 µm/sec for the given plant. In this example, a first sensor and a second sensor can be used to detect the temperature and the soil pH for the plant, respectively. The estimated cytoplasmic streaming velocity may be 45 µm/sec due to the type of soil the plant is growing in and other environmental factors measured by the sensors. The first sensor provides a temperature reading of 72.4 degrees and the second sensor provides a pH reading of 6.428. The optimal conditions from the optimal growth conditions database 430 provide the optimal temperature to be 77 degrees and the optimal soil pH to be 6.5.

After calculating a percentage differential for each condition, the temperature differential is 6% and the soil pH differential is 4.3%. In one or more embodiments of the invention, the techniques adjust the estimated cytoplasmic streaming rate by the difference percentage calculated for each iteration of sensor readings. Typically, the effect of the environmental conditions on the cytoplasmic streaming rates of respective plants creates a linear variance.

In the first temperature iteration, the cytoplasmic streaming rate from the database 430 is decreased by 6% due to the sub-optimal temperature from 50 µm/sec to 47 µm/sec. In the second pH iteration, the estimated cytoplasmic streaming rate from the first iteration is decreased by 4.3% due to the sub-optimal pH conditions from 47 µm/sec to 45 µm/sec. Based on these calculations, the current conditions yield an estimated cytoplasmic streaming velocity of 45 µm/sec, which indicates that a 5 µm/sec increase is needed to reach the optimal cytoplasmic streaming rate of 50 µm/sec for the given plant. It should be understood that additional iterations and adjustments to the estimated cytoplasmic streaming rate can occur based on the number of sensors included in the system.

The number of octaves for the current example is calculated according to Equation 2 which provides:

$$\text{Octaves} = \frac{50 \text{ µm/sec} - 45 \text{ µm/sec}}{2 \text{ µm/sec}} = 2.5 \text{ octaves}$$

According to Equation 3, the 2.5 octaves are converted to cents as shown below:

$$n = \frac{1 \text{ octave}}{1200 \text{ cents}} = \frac{2.5 \text{ octaves}}{n \text{ cents}} \rightarrow n = 3000 \text{ cents}$$

According to Equation 5, the calculated sound wave frequency is provided below:

$$b = a \times 2^{n/1200} = 46.249 \text{ Hz} \times 2^{3000/1200} = 261.626 \text{ Hz}$$

where b is equal to 261.626 Hz. In this example, the calculated sound wave frequency of 261.626 (middle C, $C^4$) provides an improvement to the current conditions of the plant by increasing the current cytoplasmic streaming rate by 5 µm/sec to reach the optimal 50 µm/sec which is the optimal cytoplasmic streaming rate indicated by the database 430. The frequency of 261.626 Hz is the optimal frequency to create a resonance in the plant to increase cytoplasmic streaming by 5 µm/sec. In one scenario, middle C may be played through the speaker within range of the plant. Alternatively, Beethoven's Symphony No. 5 can be played which is in the key of C minor (C minor is a minor scale based on C, including pitches C, D, E♭, F, G, A♭, and B♭).

Plants react differently to timbre so the quality of musical sound can impact plant growth along with frequency. In experiments, the same music on string instruments bent plants more towards the speaker versus percussion instruments. Music heavy on basses such as rap and noisy rock have been shown to damage plants similar to excess water and/or strong winds. Plants have been shown to lean away from such music and sometimes die. Experiments have shown classical and jazz music caused increased growth in plants, uniformity, with lush greens and healthy stems.

In one or more embodiments, the same process can be used on plant seeds as it has been shown that seeds that were exposed to music and later germinated produced plants that had more leaves, greater in size and improved characteristics. Plant stimulation from the music vibration can additionally aid in cell division and repair (mitosis) further increasing plant growth.

Figure 7:
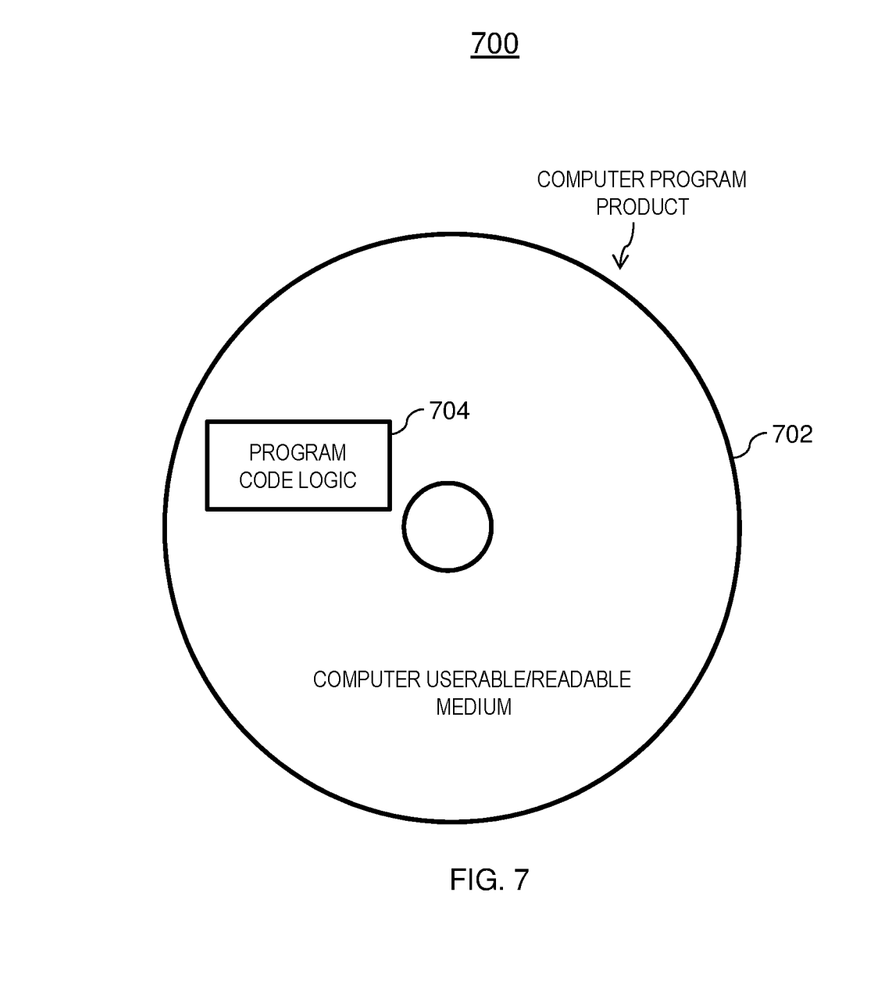
FIG. 7 depicts a computer program product in accordance with one or more embodiments of the invention.

Referring now to FIG. 7, a computer program product 700 in accordance with an embodiment that includes a computer readable storage medium 702 and program instructions 704 is generally shown. The instructions 704 implement the methods 500 and 600 as described in FIGS. 5 and 6, respectively.

The techniques described herein leverage the studies based on experiments that have been conducted to determine the optimal conditions for growing various types of plants. The studies include information about the rate of photosynthesis which is correlated to the cytoplasmic streaming occurring in the various studied plants. The vibrations provided to the plants are calculated based on the difference between the current conditions and the optimal conditions to achieve the cytoplasmic streaming for optimal photosynthesis. The calculated frequency is provided to the plant and factors in the location of the speaker to the plant, volume, above/below ground position of the speaker, etc. In addition, music can be selected that targets the calculated frequency for optimal plant growth according to the desired cytoplasmic streaming rate.

The technical benefits and effects include providing a system, device and technique to increase plant stimulation and production by calculating optimal sound wave frequencies based on current environmental conditions and plant type.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for supplementing sub-optimal environmental conditions for plant growth, the computer-implemented method comprising:
   receiving plant data for a plant;
   extracting optimal growth condition data from a database based at least in part on the plant;
   obtaining sensor data from sensors monitoring current growth conditions of the plant;
   comparing the current growth conditions of the plant to the optimal growth condition data from the database to estimate a current cytoplasmic streaming rate;
   responsive to the comparison, calculating a sound wave frequency to stimulate cytoplasmic streaming in the plant;
   transmitting the sound wave frequency to a speaker; and
   providing the sound wave frequency to the plant.

2. The computer-implemented method of claim 1, wherein the current cytoplasmic streaming rate is based at least on a percentage differential for each growth condition.

3. The computer-implemented method of claim 1, further comprising selecting, via a user, one of the sound wave frequency or music containing the sound wave frequency.

4. The computer-implemented method of claim 3, further comprising collecting plant data across multiple plants from different users and adapting the sound wave frequency or music containing the sound wave frequency based on the collected plant data across multiple plants from the different users to optimize the sound wave frequency.

5. The computer-implemented method of claim 2, wherein if the current cytoplasmic streaming rate exceeds a threshold level, selecting at least one of a sound wave frequency or music to reduce the cytoplasmic streaming rate in the plant; and wherein if the current cytoplasmic streaming rate fails to reach a threshold level, selecting at least one of a sound wave frequency or music to increase the cytoplasmic streaming rate in the plant.

6. The computer-implemented method of claim 1, further comprising updating a plant database including the current growth conditions and the sound wave frequency.

7. The computer-implemented method of claim 1, wherein the plant data is received based on capturing an image of the plant and searching a plant database using the image to identify a plant type.

8. The computer-implemented method of claim 7, further comprising monitoring the plant using an image capturing device; and
   updating the plant database according to a current state of the plant.

9. The computer-implemented method of claim 1, further comprising monitoring current audio conditions of the plant; and
   validating an operation of the speaker using a microphone.

10. The computer-implemented method of claim 1, wherein a database is formed from experimentation of cytoplasmic streaming rates for the plant in different conditions during different parts of a life cycle of the plant.

11. A system, comprising:
    one or more processors; and
    at least one memory, the memory including instructions that, upon execution by at least one of the one or more processors, cause the one or more processors to:
      receive plant data for a plant;
      extract optimal growth condition data from a database based at least in part on the plant;
      obtain sensor data from sensors monitoring current growth conditions of the plant;
      compare the current growth conditions of the plant to the optimal growth condition data from the database to estimate a current cytoplasmic streaming rate;
      responsive to the comparison, calculate a sound wave frequency to stimulate cytoplasmic streaming in the plant;
      transmit the sound wave frequency to a speaker; and
      provide the sound wave frequency to the plant.

12. The system of claim 11, wherein the current cytoplasmic streaming rate is based at least on a percentage differential for each growth condition.

13. The system of claim 11, further comprising selecting, via a user, one of the sound wave frequency or music containing the sound wave frequency.

14. The system of claim 12, wherein if the current cytoplasmic streaming rate exceeds a threshold level, selecting at least one of a sound wave frequency or music to reduce the cytoplasmic streaming rate in the plant; and wherein if the current cytoplasmic streaming rate fails to reach a threshold level, selecting at least one of a sound wave frequency or music to increase cytoplasmic streaming rate in the plant.

15. The system of claim 11, further comprising updating a plant database including the current growth conditions and the sound wave frequency.

16. The system of claim 11, wherein the plant data is received based on capturing an image of the plant and searching a plant database using the image to identify a plant type.

17. The system of claim 16, further comprising monitoring the plant using an image capturing device; and
    updating the plant database according to a current state of the plant.

18. A computer program product for supplementing sub-optimal environmental conditions for plant growth, the computer program product comprising:
    a non-transitory computer readable storage medium having stored thereon program instructions executable by a processor to cause the processor to:
      receive plant data for a plant;
      extract optimal growth condition data from a database based at least in part on the plant;

obtain sensor data from sensors monitoring current growth conditions of the plant;

compare the current growth conditions of the plant to the optimal growth condition data from the database to estimate a current cytoplasmic streaming rate;

responsive to the comparison, calculate a sound wave frequency to stimulate cytoplasmic streaming in the plant;

transmit the sound wave frequency to a speaker; and provide the sound wave frequency to the plant.

19. The computer program product of claim 18, wherein the instructions are further executable by the processor to cause the processor to:

estimate a current cytoplasmic streaming rate of the plant based on the current growth conditions, wherein if the current cytoplasmic streaming rate exceeds a threshold level, selecting at least one of a sound wave frequency or music to reduce the cytoplasmic streaming rate in the plant, and wherein if the current cytoplasmic rate streaming fails to reach a threshold level, selecting at least one of a sound wave frequency or music to increase the cytoplasmic streaming rate in the plant.

20. The computer program product of claim 18, wherein the plant data is received based on capturing an image of the plant and searching a plant database using the image to identify a plant type.

* * * * *